United States Patent [19]
Rubeling et al.

[11] Patent Number: 5,588,837
[45] Date of Patent: Dec. 31, 1996

[54] METHOD AND EQUIPMENT FOR THE FORMATION OF PROSTHETIC TOOTH STRUCTURES FOR FASTENING TO IMPLANTS

[75] Inventors: Gunter Rubeling, Bremerhaven; Burghard Otten, Misselwarden, both of Germany

[73] Assignee: Günter Rübeling, Germany

[21] Appl. No.: 373,639

[22] Filed: Jan. 11, 1995

[30] Foreign Application Priority Data

Jan. 28, 1994 [DE] Germany .......................... 44 02 511.4

[51] Int. Cl.⁶ ...................... A61C 13/12; A61C 13/225; A61C 8/00
[52] U.S. Cl. ........................... 433/172; 433/173; 433/213
[58] Field of Search ................................... 433/167, 172, 433/173, 174, 175, 176, 201.1

[56] References Cited

U.S. PATENT DOCUMENTS

| | | |
|---|---|---|
| 3,748,739 | 7/1973 | Thibert . |
| 4,085,506 | 4/1978 | Lew . |
| 4,363,627 | 12/1982 | Windeler . |
| 4,627,136 | 12/1986 | Kreylos et al. . |
| 4,767,328 | 8/1988 | Branemark . |
| 4,784,608 | 11/1988 | Mays . |
| 4,904,348 | 2/1990 | Domes et al. .............................. 204/4 |
| 4,931,016 | 6/1990 | Sillard . |
| 5,057,017 | 10/1991 | Sillard . |
| 5,227,602 | 7/1993 | Kuhn .................... 433/167 X |
| 5,246,368 | 9/1993 | Sillard . |

FOREIGN PATENT DOCUMENTS

| | | |
|---|---|---|
| 0225513 | 6/1987 | European Pat. Off. . |
| 0306864 | 3/1989 | European Pat. Off. . |
| 0498923 | 8/1992 | European Pat. Off. . |
| 3110694 | 9/1982 | Germany . |
| 3118890 | 1/1983 | Germany . |
| 3315699 | 10/1984 | Germany . |
| 4012731 | 10/1990 | Germany . |
| 4138803 | 5/1993 | Germany . |
| WO93/20774 | 10/1993 | WIPO . |

OTHER PUBLICATIONS

Ein Beitrag von P. Marcato and P. Vicino, "*Implantatgetragener Totalersatz FGP–Technik sorgt für dosierte Friktion*", (German Magazine Dental–labor, XXXIX, Edition Dec. 1991), pp. 1783 to 1788.

Primary Examiner—Nicholas D. Lucchesi
Attorney, Agent, or Firm—Merchant, Gould, Smith, Edell, Welter and Schmidt

[57] ABSTRACT

The invention is concerned with a method and an equipment for forming prosthetic tooth structures for fastening to implants, where at least one pattern is produced from the portion of a patient's jawbone containing the implants and pattern sockets of metal is arranged in it at a place which corresponds with the position of the implant in the patient's jawbone, and a prosthetic tooth structure is produced from metal with the aid of the pattern. The particular feature of the invention consists in the provision of implant electrodes of metal, the heads of which correspond essentially with the heads of the implants, being fastened releasably in the pattern sockets in lieu of dummy implants, and the pattern socket and/or the implant electrodes as well as the prosthetic tooth structure are connected to a spark erosion equipment in such a way that the pattern sockets and/or the implant electrodes form the one electrode and the prosthetic tooth structure the other electrode, and the pattern and the prosthetic tooth structure are moved one against the other, and in so doing the prosthetic tooth structure is eroded so that it is adapted to the heads of the implants.

8 Claims, 2 Drawing Sheets

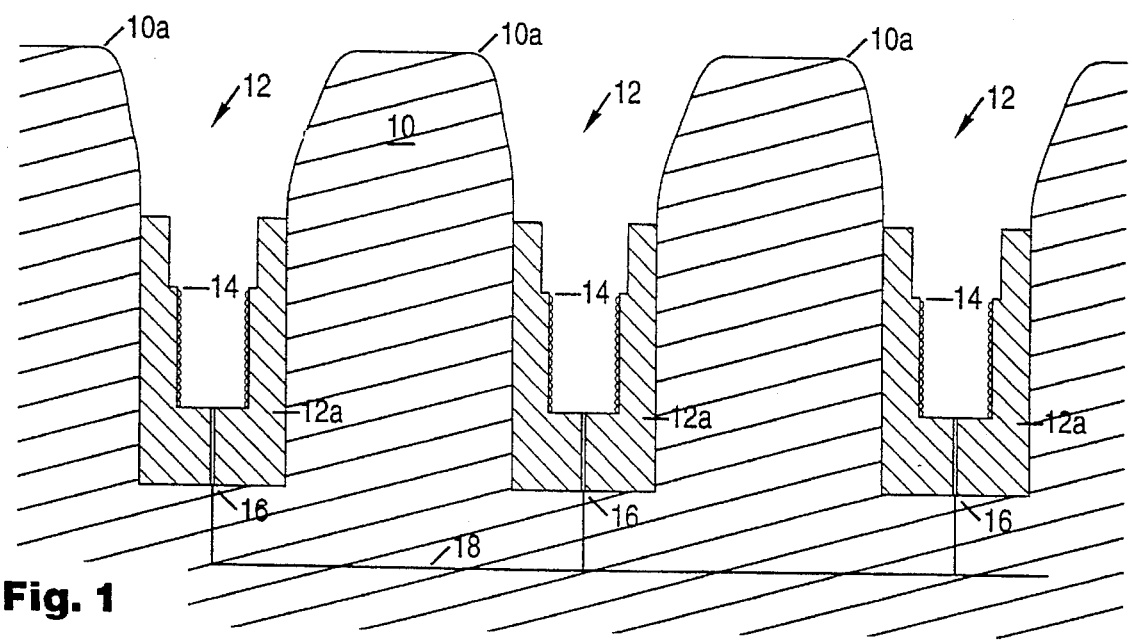
Fig. 1
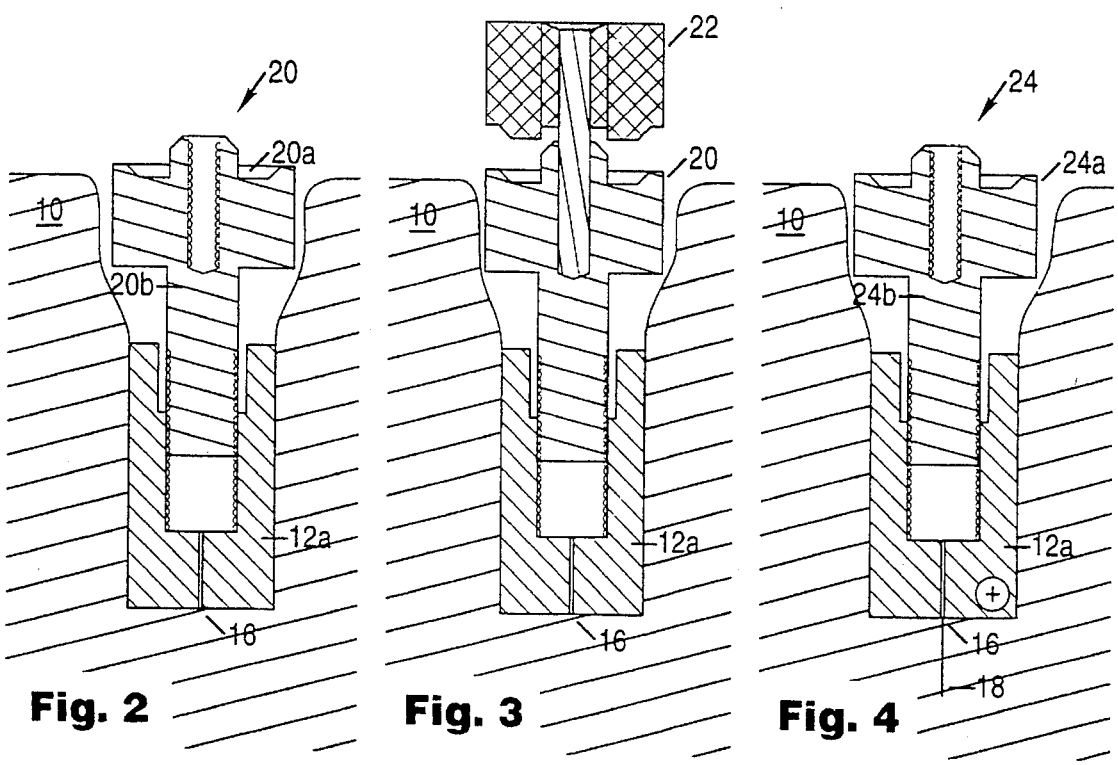
Fig. 2  Fig. 3  Fig. 4

METHOD AND EQUIPMENT FOR THE FORMATION OF PROSTHETIC TOOTH STRUCTURES FOR FASTENING TO IMPLANTS

TECHNICAL FIELD OF THE INVENTION

The invention is concerned with a method of forming prosthetic tooth structures for fastening to implants in a patient's jawbone, comprising the steps of:

producing a pattern at least from a portion of the patient's jawbone containing the implants and arranging pattern sockets of metal in it at places which correspond with the positions of the implants in the patient's jawbone;

fastening releasably into each of the pattern sockets a dummy implant, the head of which is equal to the head of the corresponding implant in the patient's jawbone;

producing a prosthetic tooth structure from metal with the aid of the pattern and the dummy implants.

The invention is further concerned with an equipment for the formation of prosthetic tooth structures for fastening to implants in a patient's jawbone, comprising pattern sockets of metal, which may be positioned in a pattern produced at least from a portion of the patient's jawbone which contains the implants, at a place corresponding with the position of the implants in the jawbone;

dummy implants which may be releasably fastened each into the pattern sockets, the head of each dummy implant being equal to the head of the corresponding implant in the patient's jawbone.

Such a method and such an equipment are disclosed for example in the German magazine "Dental Labor", XXXIX, Edition 12/91, pages 1783 to 1788 as well as in EP 498 923 A1.

One problem in the case of methods and equipments of the kind named initially consisted hitherto in that in fastening a prosthetic tooth structure to two or more implants through the technical work procedures of casting and soldering employed hitherto unavoidable stresses occurred in the structure and in the superstructure seated on it. Loadings in compression and tension thereby occurred, which again affected the osseo-integrated implants and led necessarily to the degradation of important bone substance. In the long term one had always to reckon in such cases with the loss of one or more implants.

From DE 33 15 699 A1 and DE 31 18 890 A1 there is known the use of spark erosion with the formation of prosthetic tooth structures for adjusting the support bar and the super structure to each other. DE 40 12 731 A1 discloses the production of implants by use of spark erosion.

It has been found that the known methods and apparatus are not able to achieve a seat free of stress between the implants and the prosthetic tooth structure.

SUMMARY OF THE INVENTION

It is therefore an object of the present invention to improve the method and equipment named initially, in such a way that a seat essentially free of stress may be achieved between the implants and the prosthetic tooth structure which is to be fastened onto them.

In order to achieve the above object, in accordance to the invention there is provided a method of forming prosthetic tooth structures for fastening to implants in a patient's jawbone, comprising the steps of:

producing a pattern at least from a portion of the patient's jawbone containing the implants and arranging pattern sockets of metal in it at places which correspond with the positions of the implants in the patient's jawbone;

fastening releasably into each of the pattern sockets a dummy implant, the head of which is equal to the head of the corresponding implant in the patient's jawbone;

producing a prosthetic tooth structure from metal with the aid of the pattern and the dummy implants;

fastening releasably in the pattern sockets in lieu of the dummy implants implant electrodes of metal, the head of each implant electrode essentially corresponding with the head of the corresponding implant in the patient's jawbone when taking into consideration a sparkgap of a spark erosion;

connecting the pattern sockets and/or the implant electrodes as well as the prosthetic tooth structure to a spark erosion equipment in such a way that the pattern sockets and/or the implant electrodes form the one electrode and the prosthetic tooth structure the other electrode, and moving the pattern and the prosthetic tooth structure one against the other and in doing so eroding the prosthetic tooth structure so that it is adapted to the heads of the implants in the patient's jawbone.

Furthermore, in accordance to the invention, there is provided an equipment for the formation of prosthetic tooth structures for fastening to implants in a patient's jawbone, comprising:

pattern sockets of metal, which may be positioned in a pattern produced at least from a portion of the patient's jawbone which contains the implants, at a place corresponding with the position of the implants in the jawbone;

dummy implants which may be releasably fastened each into the pattern sockets, the head of each dummy implant being equal to the head of the corresponding implant in the patient's jawbone;

implant electrodes which are manufactured from metal and may be releasably fastened in the pattern sockets in lieu of said dummy implants, the head of each implant electrode essentially corresponding to the head of the corresponding implant in the patient's jawbone when taking into consideration a sparkgap of a spark erosion; and a spark erosion equipment which is formed in such a way that the pattern sockets and/or the implant electrodes as well as a previously produced prosthetic tooth structure may be connected to it in such a way that the pattern sockets and/or the implant electrodes form the one electrode and the prosthetic tooth structure the other electrode, and the pattern and the prosthetic tooth structure are movable one against the other and in doing so the prosthetic tooth structure may be eroded in such a way that it may be adapted to the head of the implant.

With the aid of the invention it is now for the first time possible to produce a stressfree seat between implants and the prosthetic tooth structure which is to be fastened to them. In order to achieve such a gapfree and stressfree fit of the prosthetic tooth structure onto the implants, in accordance with the invention the prosthetic tooth structure is eroded onto implant electrodes which have previously been fastened into the pattern socket in lieu of the dummy implants. The head of an implant electrode corresponds to the head of the corresponding implant in the patient's jawbone when taking into consideration the sparkgap, i.e. when dimensioning the head of the implant electrode the burning-off of the electrodes is to be considered in order to achieve equal dimensions. The previously fastened dummy implants are replaced by the implant electrodes for confirmation of the prosthetic tooth structure to the implants in the patient's jawbone, since the dummy implants are made of material which is hardly erodable such that the dummy implants are not suitable for spark erosion, whereas the implant electrodes of the present invention can be produced of particular matter which is very suitable for spark erosion. Usually separate implant electrodes should be employed, through which the pattern implants previously inserted in the pattern sockets are exchanged, in order to avoid damage to the pattern implants through the process of erosion.

Through the possibility of exchanging the implant electrodes in the pattern socket during interruptions in the erosion process, they may be changed at need until an absolutely stressfree fit arises between the implants and the prosthetic tooth structures and the implant electrodes no longer exhibit any burning-off. After the erosion process the checking may be performed on pattern implants screwed into the pattern socket.

Preferably the pattern socket is provided with a slot or gap for receiving conductive material such, e.g., as wire, braid or strip for the connection to the spark erosion equipment. In the production of the pattern the conductive material is so placed in it that by means of engagement through the slot or gap in the pattern socket arranged in the pattern, an electrical contact is produced in a simple way between the conductive material and the pattern socket and hence during the erosion following later the necessary flow of current is ensured. In accordance with an advantageous further development of this execution the slot or gap is found in the foot of the pattern socket.

In accordance with a preferred embodiment of the invention, various implant electrodes are provided, which correspond with the different shapes of head obtainable from different manufacturers. The profiles of the bodies of the implant electrodes, other than the heads, are essentially the same and are matched to the pattern socket. The pattern socket accordingly exhibits a standardized inner stem which is in a position to receive implant electrodes adapted to different implant manufactures. The head of the implant electrode is always formed to correspond with the implant manufacture being processed at the time. The profile lying below the head of the implant electrode is on the contrary matched to the pattern socket. Consequently for the production of the pattern only one type of pattern socket is always employed, which has an advantageous effect upon the cost and the handling of the invention. For the rest, the same also applies for pattern implants.

Preferably, before the production of the pattern an impression is taken with an impression-pin in the patient's jawbone over the implant and the pattern socket is fastened releasably to the impression-pin. In this way it is in a particularly simpler and hence more advantageous way possible to obtain and to guarantee the original position of the implants also in the pattern.

It is useful if after the production of the pattern and before the production of the prosthetic tooth structure a dummy implant the head of which is equal to the head of the implant, is fastened releasably into the pattern socket and a built-on element, especially of plastics, is fastened releasably to the dummy implant. On built-on elements of that kind which customarily are screwed onto the pattern implant, the prosthetic tooth structure may then be modelled from, for example, wax or silicone. From the pattern of the prosthetic tooth structure so produced a mould is taken in which the prosthetic tooth structure is then cast from metal.

BRIEF DESCRIPTION OF THE DRAWINGS

A preferred embodiment of the invention is described in greater detail below with the aid of the attached drawings. There is shown in:

FIG. 1 a cross-section through a pattern with pattern sockets inserted in it;

FIG. 2 a cross-section through a pattern with a pattern socket inserted in it, into which a pattern implant is fastened;

FIG. 3 the same arrangement as in FIG. 2, with a plastics built-on element arranged on the pattern implant;

FIG. 4 a cross-section through a pattern with a pattern socket inserted in it, into which instead of the pattern socket an implant electrode is fastened.

DETAILED DESCRIPTION OF A PREFERRED EMBODIMENT

Figure 5:
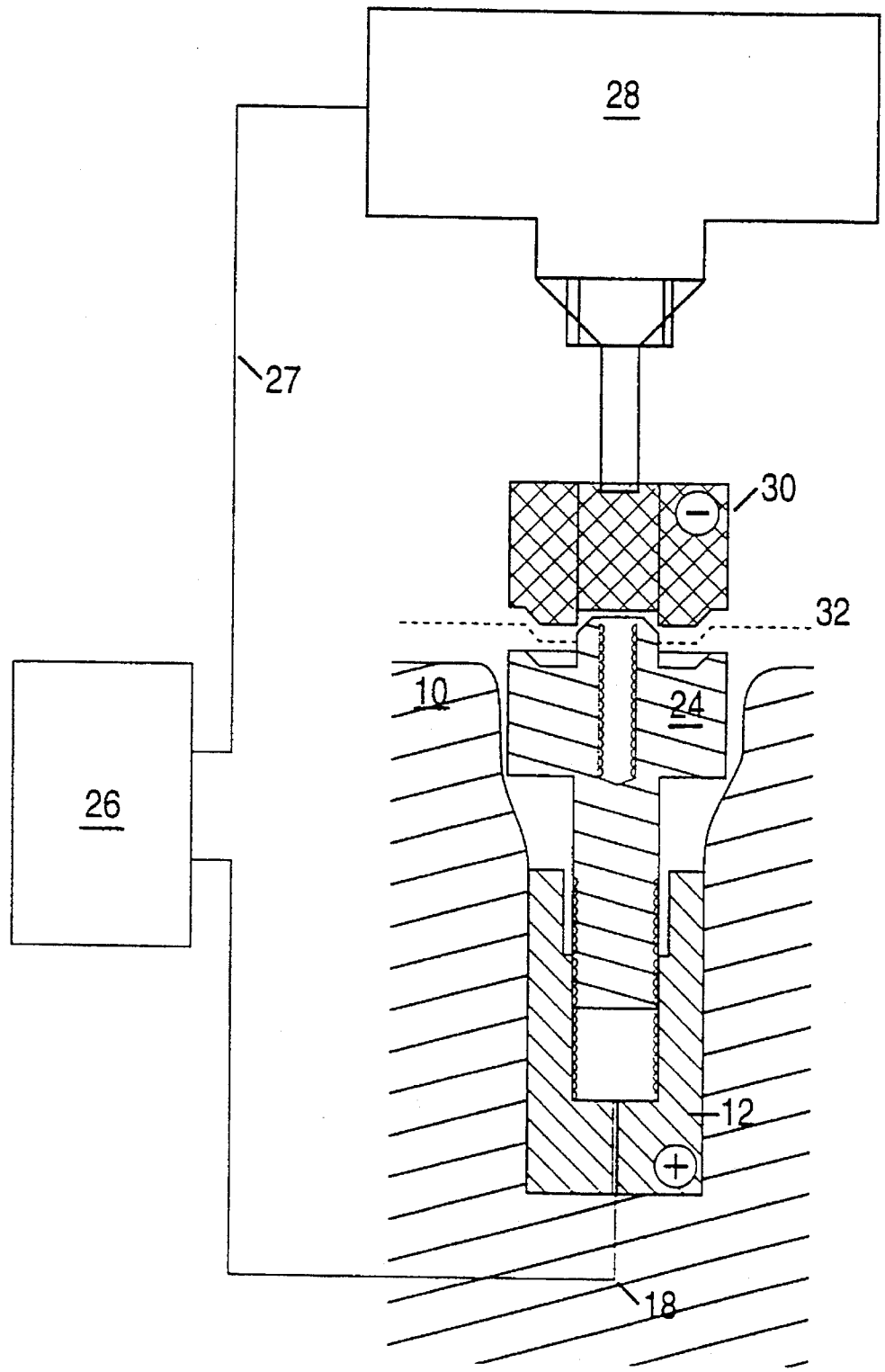
FIG. 5 diagramatically the whole arrangement of spark erosionequipment, pattern socket, implant electrode and prosthetic tooth structure during the erosion process.

In FIG. 1 a pattern 10 is represented in cross-section with a pattern socket 12 let into it.

The pattern is produced in the usual way, which for reasons of completeness is described briefly below, although the production of the pattern is not shown in the drawings.

Since the aim is to fasten a prosthetic tooth structure—where it may, for example, be a question of crowns, bridges, web constructions, prostheses or the like—to implants already existing in the jawbone, an impression of the patient's jawbone is taken at least in the region of the implants by impression-pins prescribed by the producer of the implants. After producing the impression, the pattern sockets 12 are plugged or screwed into impression-pins standing in the impression. Consequently, the pattern sockets 12 are cast into the pattern 10 when the pattern 10 is cast in the impression. It is thereby guaranteed that the pattern sockets 12 are arranged at the same places in the pattern 10 as the implants in the jawbone. In doing this it is particularly advantageous to employ low-melting-point metal for casting the pattern.

The pattern sockets 12 are produced from electrically conductive material. The inner stem 14 of the sockets 12 open to the surface 10a of the pattern 10 is so formed that standardized profile bodies to be described in greater detail below may be received. Each socket 12 exhibits at its foot 12a a slot or gap 16. In the production of the pattern 10 conductive material is introduced into this gap or slot 16, so that in the erosion yet to be described in greater detail, the necessary flow of current is guaranteed. The conductive materials employed are preferably wires, braids or copper strips: in FIG. 1 a wire 18 is shown as an example. As likewise shown in FIG. 1, the individual sockets 12 are connected together via the conductive material (wire 18) in order to be connected in common to a generator of a spark erosion equipment which is to be described in greater detail later.

In the finished-pattern 10 pattern implants 20 are then mounted on the pattern sockets 12 or respectively screwed into the pattern sockets 12 as shown in FIG. 2. Through the standardized inner stem 14 (cf. FIG. 1) the pattern sockets 12 are in a position to receive pattern implants 20 of any manufacture. The head 20a of the pattern implants 20 employed is identical in shape with the head of the corresponding implant manufacture in the patient's jawbone. The portion 20b lying under the head 20a is standardized in all of the pattern implants 20 employed here and matched to the profile of the inner stem 14 of the pattern sockets 12. When the chosen pattern implant 20 is put or screwed into the pattern socket 12, which indeed "simulates" the anchoring of the implant in the jawbone, the pattern socket 12 and the pattern implant 20 are connected into one unit, whereby a position-guided seat is guaranteed.

On the pattern implants 20 thus anchored in the pattern 10, fitting elements of plastics are then built on, which serve as a basis for the modelling of the prosthetic tooth structure. Appropriate built-on plastics elements exist for every implant manufacture. In FIG. 3, for example, the arrangement of a plastics element 22 of that kind is shown, built on the pattern implant 20.

After modelling the prosthetic tooth structure the output pattern so produced—not shown in the Figures—together with the built-on plastics elements 22 is removed from the pattern 10 of the jawbone and hence from the pattern implants 20. Subsequently an impression is taken from the output pattern in which the prosthetic tooth structure is then cast from metal. In doing so slight alterations frequently occur between the output pattern and the finish-cast structure.

In order to achieve a gapfree and stressfree fit of the prosthetic tooth structure on the pattern implants and hence upon the implants lying in the jawbone, the prosthetic tooth structure must be eroded onto the pattern implants. For doing that it is necessary to exchange the pattern implants 20 as shown in FIGS. 2 or 3 for an implant electrode 24 which is shown in FIG. 4. The implant electrode 24 has essentially the same shape as the corresponding pattern implant 20. However, the dimensions of the head 24a of the implant electrode 24 are dimensioned whilst taking into consideration the spark gap or respectively the electrode burn-off, but for the rest correspond with those of the head 20a of the pattern implant 20. Just as there are different pattern implants for the different implant manufactures, a choice may also be made between appropriate implant electrodes. As in the case of the pattern implants 20, the portion 24b lying below the head 24a is also standardized in the case of all the implant electrodes 24 available and matched to the dimensions of the inner stem 14 of the pattern socket 12. Hence after exchange of the pattern implant 20 for the implant electrode 24, no alterations at all occur within and above the pattern socket 12. The single difference—besides the already mentioned easily altered shape of the head 24a because of taking the spark gap into consideration—lies solely in the quality of the material of the implant electrode 24, which must accordingly be suited to the erosion process.

In FIG. 5 the erosion process by means of a suitable electrical spark erosion equipment is now represented diagramatically. For doing this the pattern sockets 12 are connected by means of the wire 18 to the plus pole of a generator 26 of the spark erosion equipment. Since like the pattern sockets 12 the implant electrode 24 consists of electrically conductive material and is screwed into the pattern socket 12, the voltage is applied to the implant electrode 24. A holder device 28 which likewise is part of the spark erosion equipment, is connected via another terminal lead 27 to the minus pole of the generator 26. The prosthetic tooth structure 30 is clamped in the holder device 28, that is, so that it is aligned in the direction of the pattern 10 and with the desired portions on the implant electrodes 24 and is moveable against the latter. Since the prosthetic tooth structure 30 is connected to the mounting device 28 in an electrically conductive manner, the negative potential is applied to the prosthetic tooth structure 30.

The implant electrodes 24 at one side and the prosthetic tooth structure 30 at the other are consequently connected to the spark erosion equipment in such a way that the implant electrodes 24 form the plus electrodes of the spark erosion equipment and the prosthetic tooth structure 30 forms the minus electrode of the spark erosion equipment. If the prosthetic tooth structure 30 is now moved by means of the holding device 20 up to the implant electrodes 24, spark erosion is triggered upon touching and a spark gap 32 arises, whereupon the prosthetic tooth structure 30 is eroded by the implant electrodes 24 until between the implant electrodes 24 and the prosthetic tooth structure 30 an absolutely stressfree fit exists and the implant electrodes 24 no longer exhibit any burn-off. Through the possibility of exchanging the implant electrodes 24 in the pattern sockets 12 during the erosion process, they may equally well be changed during the erosion process at need until the stressfree fit desired is achieved. Then after the erosion process the checking, for example, may be performed on the pattern implants 20 screwed into the pattern sockets 12 again.

In order to perform the erosions for this method technology, appropriate spark erosion equipments had to be developed, which have available special regulation of the power stages. This regulation sees to it that a plurality of power stages are controlled, preferably electronically, with high sensitivity in order to achieve the necessary precision and high surface quality during erosion. High-power stages are necessary in order to be able to erode gap-free and with an exact fit the high-meltingpoint alloys in the dental range, so that in particular in the case of gold, palladium, base metals and titanium erosion may be effected without any problem.

We claim:

1. A method of forming prosthetic tooth structures for fastening to implants in a patient's jawbone, comprising the steps of:

producing a pattern from a portion of the patient's jawbone containing the implants and arranging metal pattern sockets in the pattern so that positions of the pattern sockets in the pattern correspond to positions of the implants in the patient's jawbone;

releasably fastening dummy implants into each of the pattern sockets, heads of the dummy implants corresponding to heads of respective implants in the patient's jawbone;

producing a metal prosthetic tooth structure using the pattern and the dummy implants;

replacing the dummy implants with metal implant electrodes releasably fastened in the pattern sockets, heads of the implant electrodes corresponding with the heads of respective implants in the patient's jawbone when taking into consideration a sparkgap for spark erosion;

connecting the prosthetic tooth structure and either the pattern sockets or the implant electrodes to spark erosion equipment so that the prosthetic tooth structure forms a first electrode and, respectively, either the pattern sockets or the implant electrodes form a second electrode, and moving the pattern and the prosthetic tooth structure against each other so as to erode the prosthetic tooth structure so that the prosthetic tooth structure is adapted to the heads of the implants in the patient's jawbone.

2. A method as in claim 1, wherein the pattern sockets are provided with a slot or gap for receiving conductive material to form a connection to the spark erosion equipment.

3. A method as in claim 1, wherein after the production of the pattern and before the production of the prosthetic tooth structure, plastic built-on elements are releasably fastened to the dummy implants for forming the prosthetic tooth structure.

4. Apparatus for the formation of a prosthetic tooth structure for fastening to implants in a patient's jawbone, comprising:

metal pattern sockets positioned in a pattern produced from a portion of the patient's jawbone which contains the implants, and positioned in the pattern so that positions of the pattern sockets correspond to positions of respective implants in the jawbone;

a set of dummy implants adapted to be releasably fastened in the pattern sockets, each dummy implant having a head corresponding to a head of the respective implant in the patient's jawbone;

a set of metal implant electrodes adapted to be releasably fastened in the pattern sockets to replace said set of dummy implants, a head of each implant electrode corresponding to the head of the respective implant in the patient's jawbone when taking into consideration a sparkgap for spark erosion; and spark erosion equipment connectable to either the pattern sockets or the set of implant electrodes to form a first electrode and the prosthetic tooth structure connected to the spark erosion equipment to form a second electrode;

wherein moving one of the pattern and the prosthetic tooth structure against the other of the pattern and the prosthetic tooth structure results in erosion of the prosthetic tooth structure so that the prosthetic tooth structure is adapted to the head of the implant.

5. Apparatus as in claim 4, wherein the pattern sockets are provided with a slot or gap for receiving conductive material for connecting to the spark erosion equipment.

6. Apparatus as in claim 4, wherein the implant electrodes are provided with heads shaped to correspond with heads of different implants while the bodies of the implant electrodes are essentially the same and are matched to respective pattern sockets.

7. Apparatus as in claim 4, further comprising built-on elements adapted to be releasably fastened to the dummy implants for molding the prosthetic tooth structure.

8. Apparatus as in claim 7, wherein the dummy implants are provided with heads shaped to correspond with heads of different implants while the bodies of the dummy implants are essentially the same and are matched to respective pattern sockets.

* * * * *

UNITED STATES PATENT AND TRADEMARK OFFICE
CERTIFICATE OF CORRECTION

PATENT NO. : 5,588,837

DATED : December 31, 1996

INVENTOR(S) : Rubeling et al.

It is certified that error appears in the above-identified patent and that said Letters Patent is hereby corrected as shown below:

Title Page, item [22], line Filed: "Jan. 11, 1995" should read --Jan. 17, 1995--

Title Page, item [30], line Foreign Data: "44 02 511.4" should read --P44 02 511.4--

Signed and Sealed this

Twenty-eighth Day of October, 1997

Attest:

BRUCE LEHMAN

*Attesting Officer*          *Commissioner of Patents and Trademarks*